US006494872B1

(12) United States Patent
Suzuki et al.

(10) Patent No.: US 6,494,872 B1
(45) Date of Patent: Dec. 17, 2002

(54) DISPOSABLE DIAPER HAVING POCKET CONTAINMENTS AND A METHOD FOR MANUFACTURING THE SAME

(75) Inventors: Migaku Suzuki, Kanagawa; Hiroaki Fukui, Saitama, both of (JP)

(73) Assignee: Paragon Trade Brands, Inc., Norcross, GA (US)

(*) Notice: Subject to any disclaimer, the term of this patent is extended or adjusted under 35 U.S.C. 154(b) by 0 days.

(21) Appl. No.: 08/613,427

(22) Filed: Jan. 3, 1996

Related U.S. Application Data

(63) Continuation of application No. 08/068,405, filed on May 27, 1993, now abandoned.

(30) Foreign Application Priority Data

Jun. 1, 1992 (JP) ............................................ 4-140393

(51) Int. Cl.[7] .......................... A61F 13/15; A61F 13/20

(52) U.S. Cl. .......................... 604/385.26; 604/385.19; 156/164; 156/229

(58) Field of Search ................................ 156/163–164, 156/229, 494; 604/385.26, 385.19, 385.1, 385.2, 392–398

(56) References Cited

U.S. PATENT DOCUMENTS

| | | | | |
|---|---|---|---|---|
| 2,575,164 A | * | 11/1951 | Donovan | |
| 4,044,769 A | * | 8/1977 | Papajohn | |
| 4,519,800 A | * | 5/1985 | Merry | |
| 4,595,441 A | * | 6/1986 | Holvoet et al. | |
| 4,617,022 A | * | 10/1986 | Pignuel | |
| 4,675,016 A | | 6/1987 | Meuli et al. | |
| 4,726,807 A | | 2/1988 | Young et al. | |
| 4,738,677 A | | 4/1988 | Foreman | |
| 5,034,007 A | * | 7/1991 | Igaue et al. | |
| 5,110,380 A | * | 5/1992 | Ochi et al. | |
| 5,304,159 A | | 4/1994 | Tanji et al. | |
| 5,304,160 A | | 4/1994 | Igaue et al. | |
| 5,330,598 A | | 7/1994 | Erdman et al. | 156/164 |
| 5,342,342 A | | 8/1994 | Kitaoka | |
| 5,344,516 A | | 9/1994 | Tanji et al. | 156/164 |
| 5,439,459 A | * | 8/1995 | Tanji et al. | |

FOREIGN PATENT DOCUMENTS

| | | | |
|---|---|---|---|
| EP | 0508477 | * | 10/1992 |
| FR | 2617683 | * | 1/1989 |
| GB | 2266444 | | 3/1993 |
| JP | 0652241 | * | 11/1986 |
| JP | 6052242 | * | 11/1986 |
| JP | 3202057 | * | 9/1991 |
| JP | 3286761 | * | 12/1991 |

OTHER PUBLICATIONS

Vogue 2050, 1 pg, Copyright 1988.*

* cited by examiner

*Primary Examiner*—John G. Weiss
*Assistant Examiner*—K. M. Reiche
(74) *Attorney, Agent, or Firm*—Hunton & Williams

(57) ABSTRACT

The present invention is directed to provide a diaper having a pocket structure which includes a breakage-resistant hydrophobic topsheet and an apertured portion of proper size which is surrounded by a strengthened inner periphery and provides an improved leakage protection effect. The present invention is further directed to a method of manufacturing such diaper which enables economical and simplified process operation. A diaper is,provided wherein an absorbent body is interposed between a liquid impermeable backsheet and an apertured hydrophobic topsheet to form side, front and rear end portions of the diaper. The hydrophobic topsheet includes two separate sheets each having alternating concave portion and convex portions defined by a wavy side edge. The two sheets are arranged to face to each,other so that the convex portions thereof partially overlay each other at front and rear end portions of the diaper to form pocket portions. The concave portions each have a flap portion which is folded over a predetermined width to enclose an elastic member and the flap portions face each other to bound an apertured portion therebetween.

13 Claims, 5 Drawing Sheets

5 2 P 2' 5'
6 1 1' 6' 4 3 3' 2 P 2'

Fig. 5
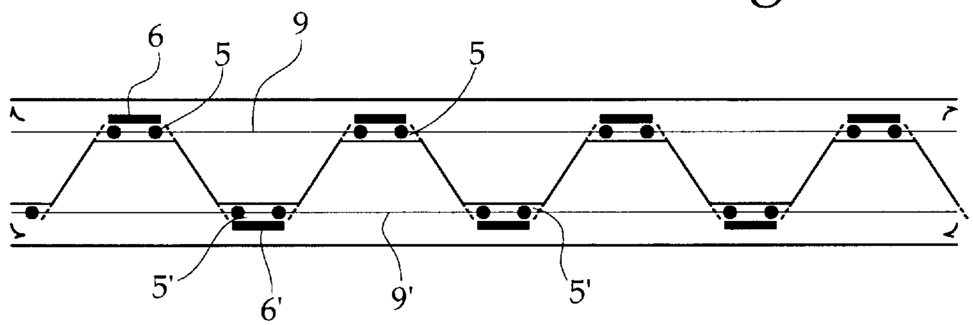
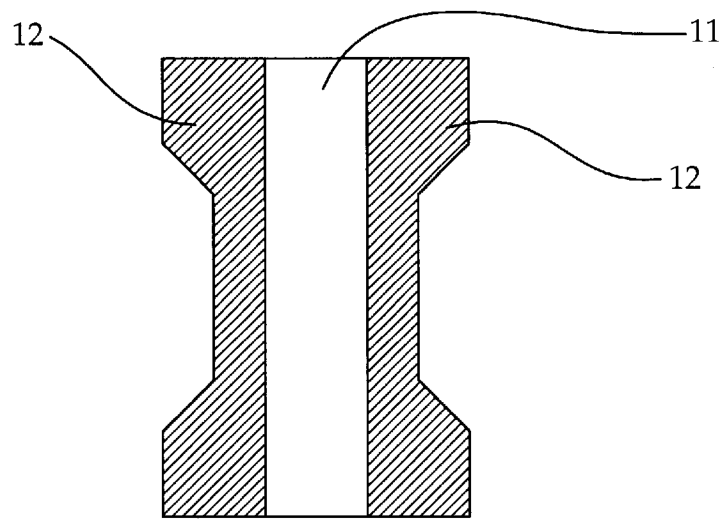
Fig. 6
Prior Art
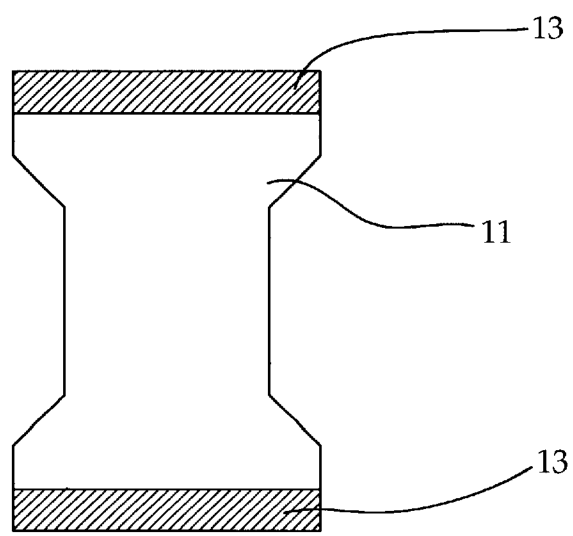
Fig. 7
Prior Art

DISPOSABLE DIAPER HAVING POCKET CONTAINMENTS AND A METHOD FOR MANUFACTURING THE SAME

This is a continuation of application Serial No. 08/068,405, filed May 27, 1993, now abandoned.

TECHNICAL FIELD

The present invention relates to improvements in baby or adult disposable diapers.

BACKGROUND OF THE INVENTION

Recent proposals for developing disposable diapers have been centered on improved urine or bowel movement leakage protection in a crotch area, front and rear waist ends.

Improved diapers have leg gathers of dual structure which comprise an inner gather and an outer gather. A topsheet accordingly comprises two different functional areas. For example, FIG. 6 illustrates such construction. A liquid-permeable topsheet 11 is positioned in a central portion of a diaper and a hydrophobic topsheet 12 is positioned in each of the opposite side portions of the diaper. Each side portion includes a leg gather.

In an effort to improve leakage protection around front and rear ends, a leakage resistant material 13, 14, such as a film, a non-woven fabric and the like, is provided in those ends as shown in FIG. 7, in association with waist gathers. This however requires a more complicated manufacturing process, and does not provide a satisfactory solution.

A new approach has been proposed that attempts to simultaneously solve leakage problems at side, front and rear ends. See, for example, Kokai Patent Sho 61-41304 and Kokai Patent Hei 3-2057.

Such approach is directed to providing side barriers and end cap barrier structures by cutting out a central portion 15 of a hydrophobic topsheet 16, as shown in FIG. 8, to connect side portions and opposite end portions.

These proposals typically make reference to a diaper having a pocket structure.

Such diapers having a pocket structure are illustrated in FIGS. 9 through 11. A liquid-permeable topsheet 18 is interposed between a liquid-impermeable backsheet 17 and a hidrophobic hydrophobic topsheet 16 having an apertured central portion 15. An absorbent body 19 backsheet 17 and the liquid-permeable topsheet 18. A space indicated by a numeral 20 is a pocket portion.

Various problems still need to be solved in order to fully enjoy the unique features of such diaper having a pocket structure.

A first problem resides in its function. Since the hydrophobic topsheet is spaced from the absorbent body 19 to form the pocket space 20, any movement and weight of a wearer is directly applied to the hydrophobic topsheet having the apertured central portion while a diaper is worn by the wearer. This causes deformation in the hydrophobic topsheet. A conventional non-woven material however generally has a relatively lower strength in a cross-direction, CD, than in a machine direction, MD, so that it is unable to sustain such influences, with the result that material breakage, tearing, or a planar displacement of the apertured central portion 15 may occur. As such planar displacement increases, the apertured central portion 15 moves outside a target zone to which urine is discharged. This causes significant problems. In order to solve these problems, it has been recommended that a material having higher strength and dimensional stability- be employed. This however adds to material cost. In order to prevent the planar displacement of the apertured portion from the target zone, the apertured portion may be made larger to accommodate such displacement. Alternatively, a stretchable material may be employed to provide the hydrophobic topsheet with freedom to conform to the movement of the wearer. However as the aperture in the apertured portion is increased, the pocket structure becomes less advantageous. The use of an elastic material for the hydrophobic topsheet increases the material cost.

A second problem resides in the manufacturing process for the diaper. In order to form the pocket structure, it is required that the size of the hydrophobic topsheet be formed to correspond with the size of the wearer, prior to cutout of the aperture 15. Incomplete cutting undesirably leaves the hydrophobic nonwoven material at the central portion of the diaper. Such a defective diaper has no commercial value. Therefore, not only is a highly precise cutting operation required, an investment for installing such cutting equipment renders the process very expensive. Further, cutout nonwoven portions are not reusable and treated as waste so that an increased amount of material is disadvantageously required.

SUMMARY OF THE INVENTION

The present invention is directed to reduce the material waste of the hydrophobic topsheet material and further to enlarge the size of the apertured portion. The present invention is further directed to improve leakage protection and to increase strength around the periphery of the apertured portion by placing an elastic material around the apertured portion.

In accordance with the present invention, there is provided a diaper having a pocket structure wherein an absorbent body is interposed between a liquid-impermeable backsheet and an apertured hydrophobic topsheet to form front and rear waist end portions and side crotch portions of a diaper. The hydrophobic topsheet comprises two separate sheets each having a concave portion and convex portions. The two sheets are arranged to face each other so that respective convex portions thereof partially overlay each other at front and rear end portions of the diaper to form pocket portions. A concave edge portion of each sheet is folded over by a predetermined width to enclose an elastic member so that the folded-over portions that face each other define an apertured portion therebetween.

BRIEF DESCRIPTION OF THE DRAWINGS

The above-described elements which constitute the present invention will now be explained.

FIG. 5 is an explanatory view illustrating still another embodiment of the present manufacturing method.

FIG. 6 is an explanatory view illustrating a prior art diaper construction.

FIG. 7 is an explanatory view showing a prior art diaper construction.

DESCRIPTION OF A PREFERRED EMBODIMENT

In an absorbent garment, such as a disposable diaper, a backsheet (17 in FIG. 11) forms an outermost layer of the diaper and may be comprised of liquid leakage-proof material such as polyethylene film or polyethylene/non-woven composite material, to prevent leakage of liquid discharges absorbed by the diaper.

Figure 10:
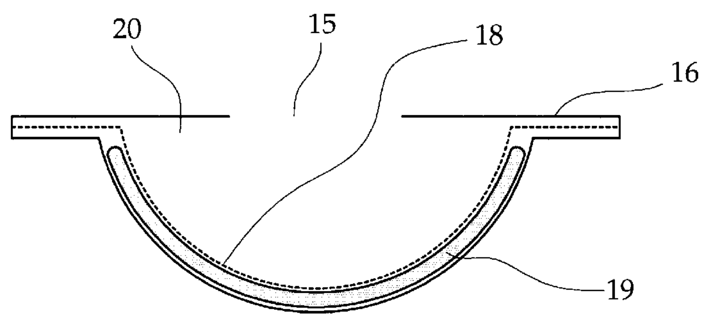
FIG. 10 is an enlarged cross-sectional view along a line I—I of FIG. 9.

The absorbent body is a portion which draws and stores the discharges like a storage tank, and comprises an absorbent material generally comprising a liquid permeable top layer (18 in FIG. 10), a diffusion sheet such as a tissue paper, wood pulp and superabsorbents (19 in FIG. 10). The top layer may be optionally omitted from the absorbent body.

The hydrophobic topsheet (16 in FIG. 10) is a portion which overlays the absorbent body and directly contacts the wearer's skin. Diacharges from the wearer move toward and are trapped by the apertured portion of the topsheet. Since the wearer's body contacts this hydrophobic topsheet, a suitable material may be a non-woven fabric which is soft, compliant and minimally irritating to skin. For the purpose of preventing strike-back of the discharge from the absorbent body, it is desired to use non-woven material which comprises hydrophobic fibers such as polypropylene (PP), polyester (PET), or polyethylene (PE).

It is further preferred to use a completely liquid impermeable sheet such as a non-woven/PE film laminate or a nonwoven/PP film laminate.

In accordance with the present invention, the apertured portion is not a cutout portion made in a single sheet, but is formed by combining two separate sheets each having concave side edge portions and convex side edge portions and partially overlaying the convex portions thereof. The overlaid convex portions may be entirely secured. Alternatively, they may be partly secured to each other so that they are slidable with to each other to freely move in response to the movement of the wearer without causing any substantial displacement of the apertured portion. A higher extent of strength is not required to resist breakage.

According to another aspect of the present invention, a portion of the concave side edge portion is folded over by a predetermined width and the folded-over portion retains an elastic member so that an upstanding gather structure is provided when the elastic element contracts. Such upstanding gather structure forms a barrier wall against transverse liquid flow to reduce leakage of the diaper. Such structure also has increased resistance to tearing or breaking The elastic member may extend beyond the folded-over portion toward the front end and/or the rear end of the diaper.

Characteristic features of the present manufacturing method reside in the cutting procedure for the hydrophobic topsheet and its elastic member attachment. These two features will be described below.

A continuous topsheet material is subjected to cutting along a longitudinally-extending S-shaped cutting line to provide two sheets each having alternating convex and concave portions. Extra transverse cuts are made beyond the concave edge portions to provide flap portions. A longitudinally extending elastic member is placed on, or outwardly of a proximal end of each flap portion. The flap portion is then folded over to enclose the elastic member and to strengthen the folded portion.

One of the two separated sheets is longitudinally offset with respect to the other sheet so that convex portions of the two separated sheets partially overlay each other and the concave portions of the two sheets are disposed in facing relation to each other to define therebetween an apertured portion bounded by the elastic members. The partially overlaid convex portions may be partly secured to each other to the extent that such securement still leaves some freedom for them to move relative to each other.

This assembly produced from the re-joined sheets is secured over absorbent bodies which are intermittently placed on a hydrophobic backsheet at a regular interval. Consecutive spaced apart transverse cuts made thereto produce individual diapers each having a desired length extending between front and rear waist ends. The folding operation of the flap portions may be mechanically performed. Alternatively, a continuous string or tape may be longitudinally secured on the flap portions along the elastic member. The flap portions will be folded using the string or tape through an arc of 180° about a folding line. The elastic member itself may be utilized-as such folding means.

Examples will be now explained hereinafter in conjunction with the drawings.

Figure 1:
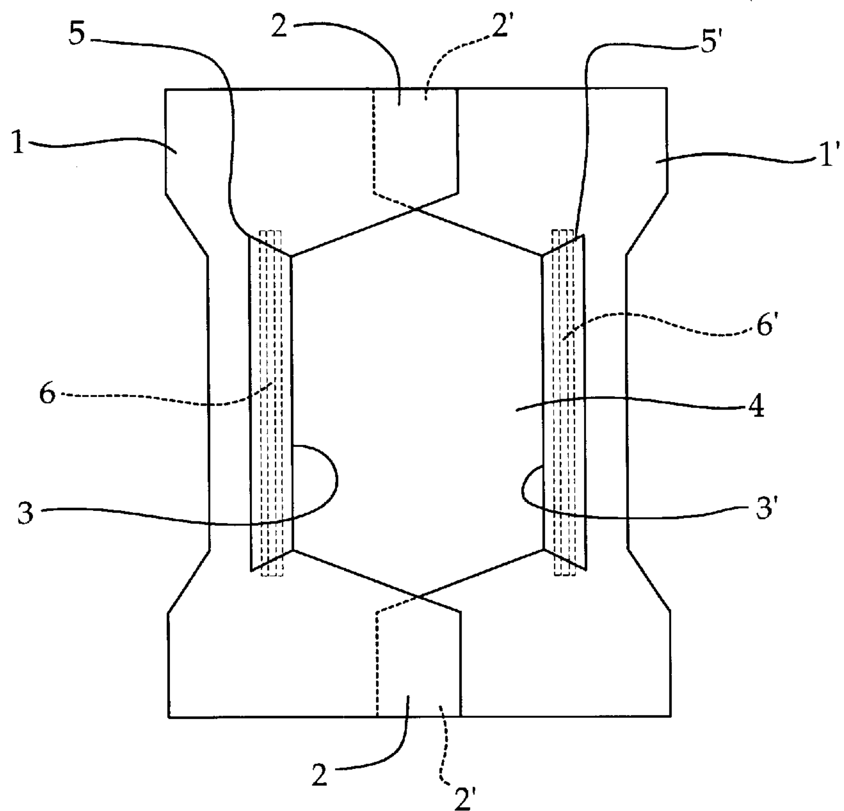
FIG. 1 is a plan view of a diaper embodiment in accordance with the present invention.
Figure 9:
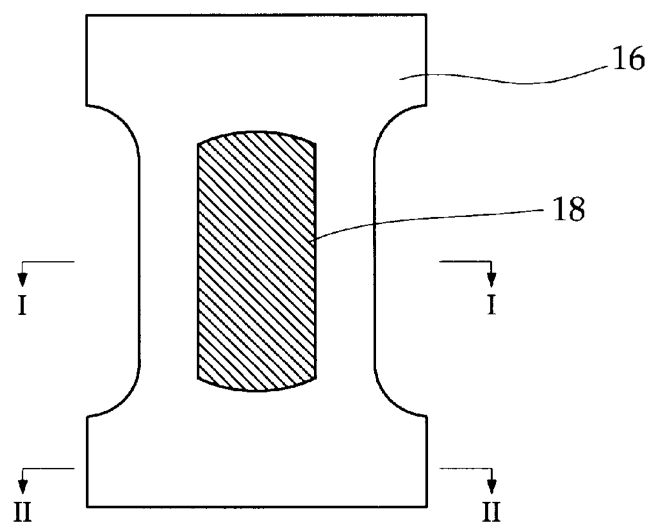
FIG. 9 is a plan view of a prior art diaper.
Figure 11:
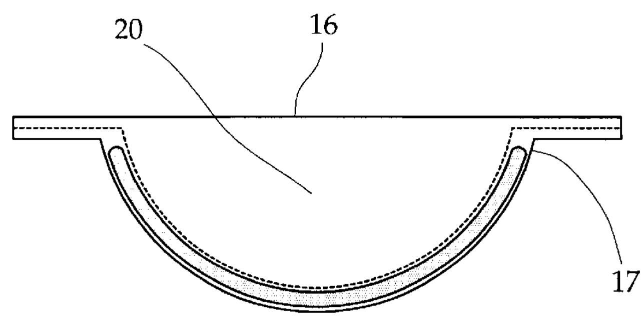
FIG. 11 is an enlarged cross-sectional view along a line II—II of FIG. 9.

FIG. 1 is a plan view of a diaper produced according to a preferred embodiment of the present invention which includes an absorbent body and a backsheet configured similarly to those as illustrated in FIGS. 9–11.

Referring to FIG. 1, reference numerals 1, 1' indicate left and right hydrophobic topsheets. The left hydrophobic topsheet 1 includes two convex portions 2, 2 and a concave portion 3 between the two convex portions 2, 2. The right hydrophobic topsheet 1' includes two convex portions 2', 2'and a concave portion 3' between the two convex portions 2', 2'.

The convex portions 2, 2' are partially overlaid over each other at front and rear waist end portions. The concave portions 3, 3' of the two topsheets 1, 1' are disposed in facing relation and are spaced from each other to define an apertured portion, or opening, 4 therebetween. Concave flap portions.of the concave portions 3, 3' include folded over portions 5, 5' which enclose elongate elastic members 6, 6'.

Figure 2:
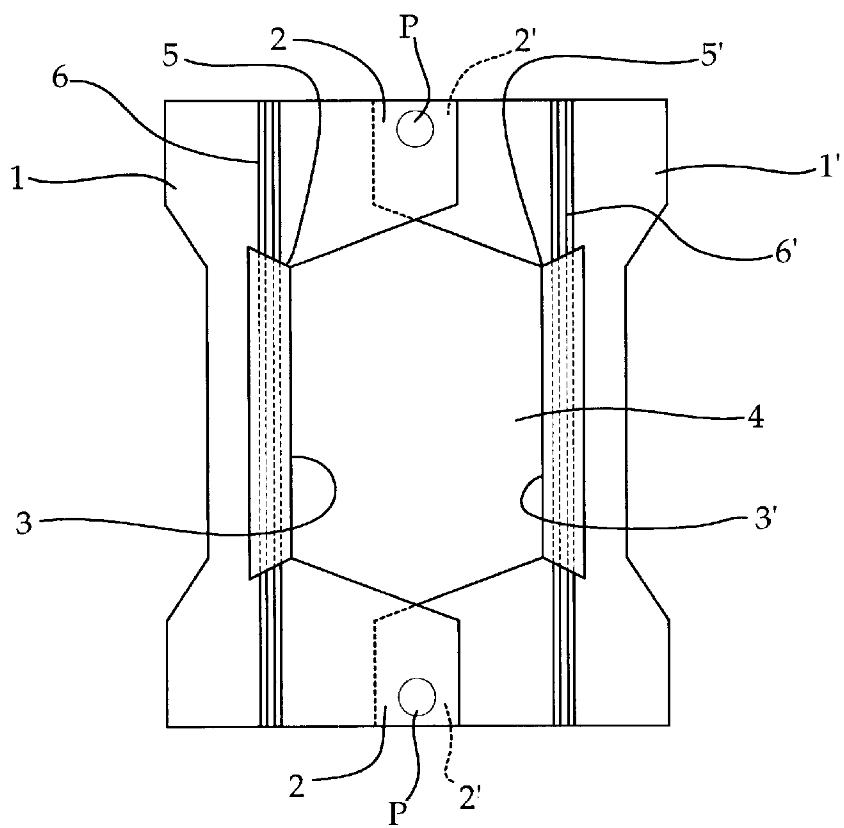
FIG. 2 is a plan view of another diaper embodiment in accordance with the present invention.

FIG. 2 shows another diaper embodiment in accordance with the present invention wherein the same numerals as those in FIG. 1 indicate the same elements. The difference from the first embodiment is that the elastic members 6, 6' extend all the way to the front and rear waist ends in this garment. This configuration provides strengthened sides surrounding the apertured portion, or opening, 4 and improved leakage resistance. The convex portions 2, 2' are secured to each other at P but are free to move with respect to each other to some extent and the apertured portion, or opening, 4 is protected from being opened up excessively by any incidental forces.

A manufacturing method to produce such disposable garments will now be explained. Since an absorbent body, backsheet and the like are manufactured by conventional methods, the focus of the following description will be placed on production of the hydrophobic topsheet.

Figure 3A:
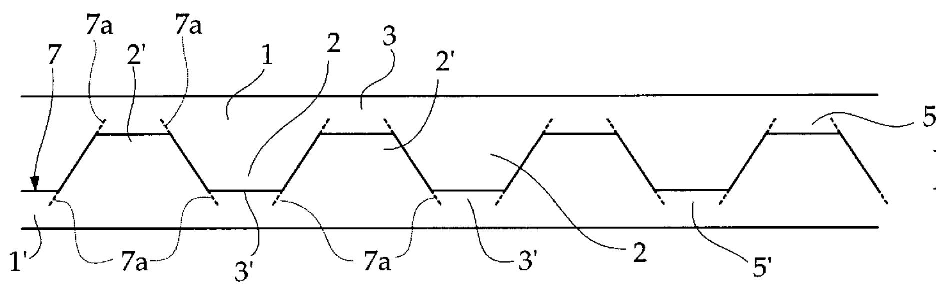
FIGS. 3*a*, 3*b*, 3*c*, 3*d* provide an explanatory sequential view illustrating a manufacturing method.

As illustrated in FIG. 3*a*, a longitudinally-extending expanse of hydrophobic topsheet material 1 is longitudinally cut along a cutting line 7 so that separate first and second topsheet members (1, 1') are formed. Each topsheet member has alternating convex portions 2, 2' and concave portions 3, 3', respectively. It should be noted here that each convex portion 2 of the first topsheet member 1 is contiguous, transversely neighbors, or faces the concave portion 3 of the second topsheet member 1'.

Figure 3B:
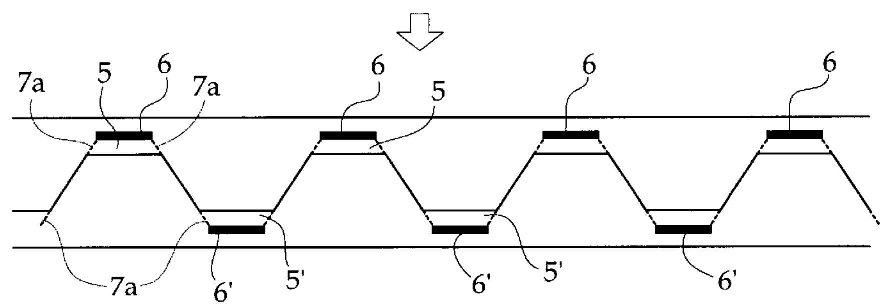

Simultaneously with cutting along line 7, additional transverse cuts, as illustrated by dotted lines 7*a*, are produced in the topsheet material members 1, 1', which cuts extend outwardly from and are spacedapart along the transverse cutting line portion of the cutting line 7 to produce flap portions 5, 5' respectively. Elastic members 6, 6' are secured, as by adhesive bonding or other known securing means, in concave portions 3, 3' respectively between converging transverse cutting lines 7*a*, as shown in FIG. 3*b*. Each flap portion 5, 5' is folded over and secured onto the topsheet material 1, 1' respectively so that,the elastic members 6, 6' respectively are enclosed, or sandwiched, therebetween, as shown in FIG. 3*d*.

Figure 3C:
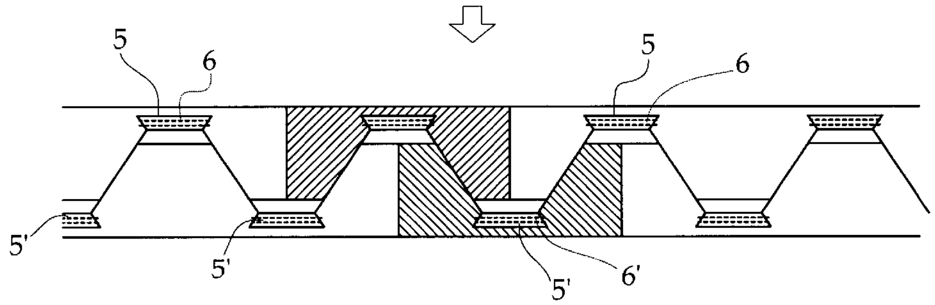
Figure 3D:
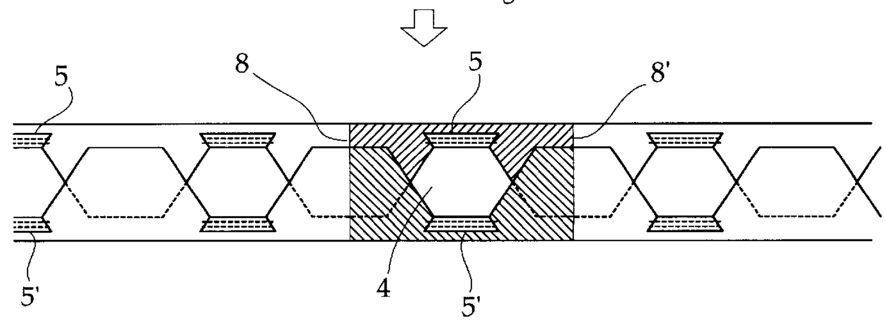

The cross-hatched portions in the first and second topsheet memberes in FIG. 3*c* indicate those portions required to constitute one hydrophobic topsheet unit of an individual diaper. The first and second topsheet members 1, 1' are longitudinally offset relative to each other to the positions illustrated in FIG. 3*d*. In this position the cross-hatched portions are aligned transversely so that concave portions 3, 3' thereof are disposed in facing relation and spaced from each other to define the apertured portion, or opening, 4.

This assembly is then combined with the other diaper components including the backsheet and the absorbent body to form a continuous diaper unit which is transversely cut at along the lines 8, 8' to produce individual diapers.

Figure 4:
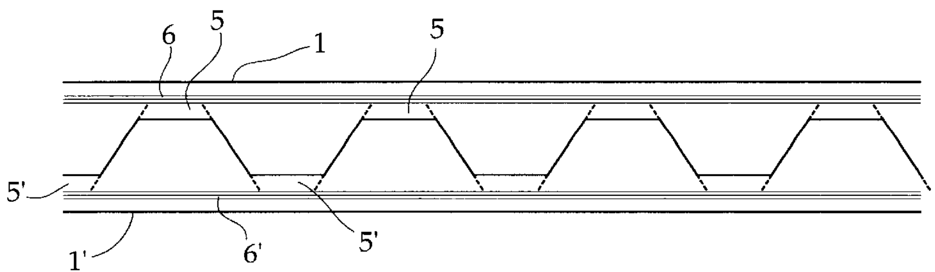
FIG. 4 is an explanatory view illustrating another embodiment of the present manufacturing method.
Figure 8:
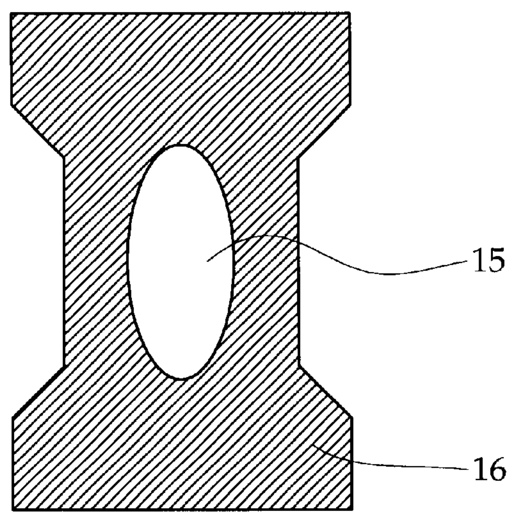
FIG. 8 is an explanatory view showing a prior art diaper construction.

FIG. 4 illustrates another example. Continuous elastic strands 6, 6' are longitudinally secured along the first and second topsheet members and are spaced a distance inwardly from the outer side margins of the topsheet members 1, 1' respectively. Flap portions 5, 5' are then folded over for securement over the elastic strands 6, 6' respectively. A diaper manufactured by this method includes elastic members which longitudinally extend over the crotch portion and between the front and rear end portions. This feature further reduces the leakage of the topsheet.

FIG. 5 illustrates still another example of the present invention. Strands 9, 9' are longitudinally placed and spot-bonded to flap portions 5, 5', respectively, before or after the step shown in FIG. 3*b*. These strands 9, 9' are folded about their longitudinal axes through an arc of 180° to fold the flap portions 5, 5' onto the elastic members 6, 6'respectively. The elastic members 6, 6' may be employed as substitutes for the strands 9, 9'.

It is to be understood that any proper variations may be conveniently made to the configurations or shapes of the longitudinal and transverse cutting lines as described in the above examples.

The present invention provides a diaper which requires no material waste of the hydrophobic topsheet. Since the diaper includes elastic material surrounding the apertured portion, improved leakage protection and strengthened inner peripheries are provided. The present invention further provides a method of manufacturing the diaper which enables a higher production rate and a simplified process operation.

We claim:

1. A diaper having a liquid impermeable backsheet, a hydrophobic topsheet, and an absorbent body interposed between said backsheet said topsheet to form sides and front and rear end portions of said diaper, said hydrophobic topsheet comprising two separate sheets each having a concave portion between spaced convex portions, said two sheets being arranged to face each other so that said convex portions thereof partially overlay each other at said front and rear end portions of the diaper to form pocket portions, said concave portions each having a pair of spaced transverse cuts therein to define a flap portion which is folded over by a predetermined width to enclose an elastic member whereby said folded-over flap portions face each other to define an apertured portion therebetween.

2. The diaper of claim 1, wherein:

said overlaying convex portions are secured so that said convex portions are movable with respect to each other to accommodate movement of a wearer.

3. A method for manufacturing a diaper having pocket portions comprising the steps of:

providing an elongate continuous expanse of hydrophobic topsheet material;

cutting said topsheet material along a wavy line extending longitudinally of the topsheet material to provide first and second continuous sheet members each having alternating convex portions and concave portions;

producing a pair of spaced transverse cuts in each of said concave portions of said topsheet material of a predetermined length which extend into each of said concave portions to form flap portions;

positioning an elongate elastic member on a topsheet member in the region of said concave portion adjacent a flap portion;

folding over said flap portion to enclose said elastic member;

longitudinally offsetting said first and second continuous sheet members with respect to each other so that said convex portions thereof partially overlay each other and said concave portions thereof face each other and are spaced from each other to define an apertured portion therebetween;

interposing absorbent bodies between a backsheet and said offset first and second continuous sheet members;

bonding said backsheet with said first and second continuous sheet members at sides and front and rear portions of an individual diaper section intended to be cut out therefrom so that pocket portions are provided by said hydrophobic topsheet material and said apertured portion is defined between said folded-over flap portions of said concave portions; and producing transverse cuts at said front and rear end portions to separate an individual diaper section.

4. The method of claim 3, wherein:

said overlaying convex portions are secured so that said convex portions are moveable with respect to each other to accommodate movement of a wearer.

5. A disposable diaper comprising a liquid impermeable backsheet, an absorbent body overlying said backsheet, an elongate hydrophobic topsheet overlying said absorbent body, said topsheet comprising two separate sheets each having longitudinally spaced-apart convex portions and a concave portion therebetween, said two sheets being disposed adjacent opposite sides of said absorbent body and in facing relation, with the convex portions at one set of ends of said sheets overlapping and the convex portions at another set of ends of said sheets opposite said one set of ends overlapping, and the concave portions facing and spaced from each other to pocket portions, said concave portions each having a flap portion defined by a pair of spaced-apart cuts extending outwardly from said pocket portions, and each of said sheets having an elastic member extending longitudinally of said sheet secured to said concave portion of the sheet adjacent said pocket portions, said flap portion of the sheet being folded over by a predetermined width outwardly from said pocket portions and secured over said elastic member to enclose said elastic member whereby said folded-over flap portion bounds [one] a side of said pocket portions.

6. The diaper of claim 5, wherein said elastic member is contractible to define an inner gather to provide formed fit for a wearer.

7. The diaper of claim 6, wherein the concave portion has a first predetermined length and wherein said elastic member has a length substantially equivalent to said first predetermined length.

8. The diaper of claim 6, wherein the topsheet has a second predetermined length and wherein said elastic member has a length substantially equivalent to said second predetermined length.

9. A method for manufacturing a disposable diaper having pocket portions comprising the steps of:

providing an elongate continuous expanse of hydrophobic topsheet material, cutting said topsheet material along a wavy line extending longitudinally of the topsheet material to provide first and second continuous sheet members each having alternating convex portions and concave portions, producing longitudinally spaced-apart transverse cuts in each of said concave portions of said topsheet material of a predetermined length which extend into each of said concave portions to form flap portions, securing an elongate elastic member on a topsheet member adjacent a flap portion, folding over said flap portion to enclose said elastic member and securing said flap portion in its folded-over position, longitudinally offsetting said first and second continuous sheet members with respect to each other so that said convex portions thereof partially overlay each other and said concave portions face each other and are spaced from each other to define an apertured portion therebetween, providing a substantially continuous expanse of backsheet material adjacent and in facing relation to said first and second sheet members, interposing absorbent bodies between said overlapping first and second continuous sheet members and said backsheet material, bonding said backsheet with said first and second continuous sheet members at sides and front and rear end portions of an individual diaper section intended to be cut out therefrom so that pocket portions are provided by said hydrophobic topsheet material and said apertured portion is defined between the folded-over flap portions of said concave portions, and producing transverse cuts at said front and rear end portions to separate an individual diaper section.

10. The method of claim 9, which further comprises the step of securing an elongate member to said flap portion intermediate an inner edge of said concave portion and said elastic member, and using said elongate member to fold said flap portion over said elastic member.

11. The method of claim 9, wherein said elastic member has a length substantially equivalent to a distance by which said spaced apart transverse cuts in each of said concave portions are separated, said elastic member also being positioned between said transverse cuts.

12. The method of claim 9, wherein at least one of said continuous topsheet members has a third predetermined length and wherein said elastic member has a length substantially equivalent to said third predetermined length and extends substantially the full length of said at least one of said continuous topsheet members.

13. A method for manufacturing a disposable diaper having pocket portions comprising the steps of:

providing an elongate continuous expanse of hydrophobic topsheet material, cutting said topsheet material along a wavy line extending longitudinally of the topsheet material to provide first and second continuous sheet members each having alternating convex portions and concave portions, producing longitudinally spaced-apart secondary transverse cuts in each of said concave portions of said topsheet material of a predetermined length which extend into each of said concave portions to form flap portions, securing an elongate elastic member on a topsheet member adjacent a flap portion, securing an elongate member to said flap portion intermediate an inner edge of said concave portion and said elastic member, and using said elongate member to fold said flap portion over said elastic member and securing said flap portion in its folded-over position, longitudinally offsetting said first and second continuous sheet members with respect to each other so that said convex portions thereof partially overlay each other and said concave portions face each other and are spaced from each other to define an apertured portion therebetween, providing a substantially continuous expanse of backsheet material adjacent and in facing relation to said partially overlaying first and second continuous sheet members, interposing absorbent bodies between said first and second continuous sheet members and said backsheet material, bonding said backsheet with said first and second continuous sheet members at sides and front and rear end portions of an individual diaper section intended to be cut out therefrom so that pocket portions are provided by said hydrophobic topsheet material and said apertured portion is defined between the folded-over flap portions of said concave portions, and producing transverse cuts at said front and rear end portions to separate an individual diaper section.

* * * * *